United States Patent
Donnola et al.

(10) Patent No.: US 11,286,254 B2
(45) Date of Patent: Mar. 29, 2022

(54) PROCESS FOR THE SYNTHESIS OF 2-BENZHYDRYL-3 QUINUCLIDINONE

(71) Applicant: Procos S.P.A., Cameri (IT)

(72) Inventors: Monica Donnola, Novara (IT); Matteo Mossotti, Carpignano Sesia (IT); Mauro Barbero, Villata (IT); Jacopo Roletto, Turin (IT); Paolo Paissoni, Druento (IT)

(73) Assignee: Procos S.P.A., Cameri (IT)

( * ) Notice: Subject to any disclaimer, the term of this patent is extended or adjusted under 35 U.S.C. 154(b) by 56 days.

(21) Appl. No.: 16/760,324

(22) PCT Filed: Oct. 30, 2018

(86) PCT No.: PCT/EP2018/079675
§ 371 (c)(1),
(2) Date: Apr. 29, 2020

(87) PCT Pub. No.: WO2019/086434
PCT Pub. Date: May 9, 2019

(65) Prior Publication Data
US 2020/0339561 A1 Oct. 29, 2020

(30) Foreign Application Priority Data
Oct. 30, 2017 (IT) .................. 102017000123558

(51) Int. Cl.
*C07D 453/02* (2006.01)

(52) U.S. Cl.
CPC .................. *C07D 453/02* (2013.01)

(58) Field of Classification Search
CPC .................................. C07D 453/02
See application file for complete search history.

(56) References Cited

U.S. PATENT DOCUMENTS

| | | |
|---|---|---|
| 3,560,510 A | 2/1971 | Warawa |
| 5,716,965 A * | 2/1998 | Ito .................. C07D 453/02 514/305 |

OTHER PUBLICATIONS

Howson W. et al., "An SAR study for the non-peptide substance P receptor (NK1) antagonist, CP-96, 345", Bioorganic & Medicinal Chemistry Letters, Pergamon, Amsterdam, NL, vol. 2 No. 6, Jan. 1, 1992, pp. 559-564.
Search Report and Written Opinion of PCT/EP2018/079675 dated Dec. 17, 2018.
Viti G. et al., "Synthesis of a benzo[b]-1,5-naphthyridine derivative as a potential constrained NK1 receptor antagonist", Tetrahedron Letters, vol. 35, No. 32, Aug. 1, 1994, pp. 5939-5942.
Warawa E.J. et al. "Excerpta medica. Section 23: Nuclear medicine", Journal of Medicinal Chemistry, Jan. 1, 1974, pp. 497.

* cited by examiner

*Primary Examiner* — D Margaret M Seaman
(74) *Attorney, Agent, or Firm* — Silvia Salvadori, P.C.; Silvia Salvadori

(57) ABSTRACT

The present invention discloses a process for the preparation of 2-benzhydryl-3-quinuclidinone (1). (I). The process of the invention allows to obtain the intermediate 2-benzhydryl-3-quinuclidinone (1) by reaction of 2-benzylidene-3-quinuclidinone (2) with the Grignard reagent phenyl-magnesium halide, in particular chloride or bromide, in the presence of catalytic amounts of copper (I) salts. Taking advantage of the high efficiency of the catalytic system of the copper (I) salts, 2-benzhydryl-3-quinuclidinone (1) is obtained in higher yields than those of the known processes. Advantageously, since the amounts of copper (I) salts are catalytic, the latter can easily be removed from the reaction mixture, and the process is carried out in the presence of solvents less toxic and expensive than those used in the state of the art.

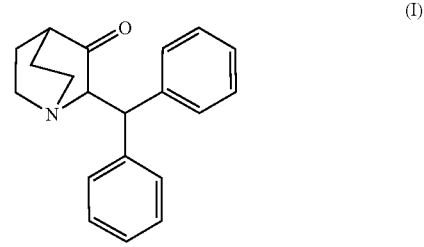

(I)

7 Claims, No Drawings

PROCESS FOR THE SYNTHESIS OF 2-BENZHYDRYL-3 QUINUCLIDINONE

This application is a U.S. national stage of PCT/EP2018/079675 filed on 30 Oct. 2018, which claims priority to and the benefit of Italian Application No. 102017000123558 filed on 30 Oct. 2017, the contents of which are incorporated herein by reference in their entireties.

FIELD OF THE INVENTION

The present invention relates to a process for the synthesis 2-benzhydryl-3-quinuclidinone.

BACKGROUND OF THE INVENTION

The compound 2-benzhydryl-3-quinuclidinone is a key intermediate for a series of antagonists of the NK1 receptor, which is widely distributed in the central and peripheral nervous system of the mammals. Examples of NK1 antagonists comprise the compounds CP96345 and L703606, discovered by Pfizer at the beginning of 90's of the last century, and Maropitant, a potent antiemetic used for the motion sickness in pets.

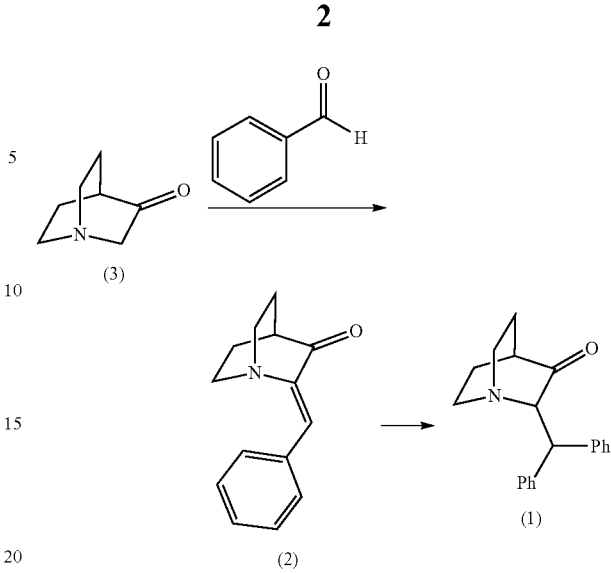

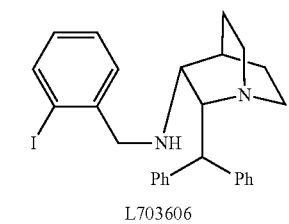

L703606

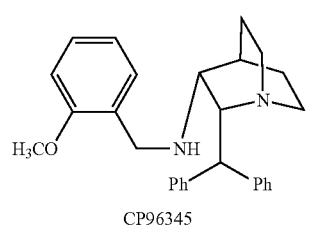

CP96345

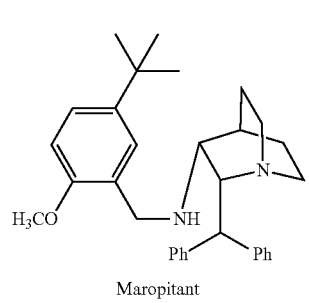

Maropitant

The literature concerning the preparation of 2-benzhydryl-3-quinuclidinone (1) is rather limited: the key intermediate is always obtained in yields very poor and never exceeding 50% through two synthetic steps starting from 3-quinuclidinone (3).

U.S. Pat. No. 3,560,510 discloses the preparation of 2-benzhydryl-3-quinuclidinone (1) starting from 2-benzylidenyl-3-quinuclidinone (2) through a Michael reaction in the presence of the Grignard reagent phenylmagnesium bromide and using benzene as solvent. The yield is not higher than 50%.

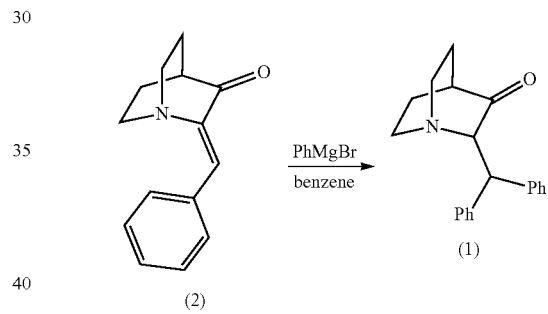

In Organic Process Research & Development 2006, 10, 142-148 the same synthetic procedure described in U.S. Pat. No. 3,560,510 is reported, using phenylmagnesium chloride and THF.

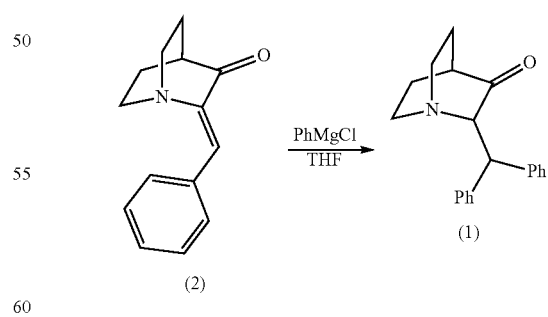

European Journal of Medicinal Chemistry 119 (2016) 231-249 describes the synthesis of 2-benzhydryl-3-quinuclidinone (1) starting from 2-benzylidenyl-3-quinuclidinone (2) in the presence of copper (I) salts. The intermediate is obtained through a Michael addition with copper (I) iodide, used in equimolar amount to the 2-benzylidenyl-3-quinuclidinone (2) and to phenylmagnesium chloride; the reaction is carried out in benzene and the desired product is obtained in very low yields (3%).

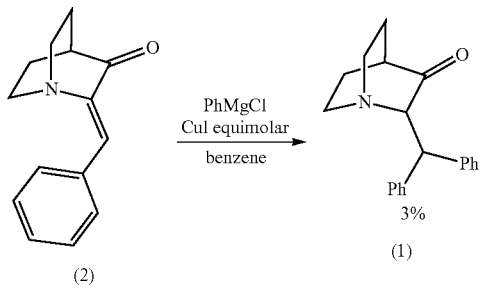 [SMILES: O=C1/C(=C/c2ccccc2)N2CCC1CC2 ; "PhMgClCul equimolar" ; O=C1C2CCN(CC2)C1C(c1ccccc1)c1ccccc1]

DISCLOSURE OF THE INVENTION

It has now been found that 2-benzhydryl-3-quinuclidinone (1) can be obtained in high yields exploiting the high efficiency of copper (I) salts used in catalytic amount.

Therefore, the object of the present is a process for the preparation of 2-benzhydryl-3-quinuclidinone (1) comprising the reaction of 2-benzylidene-3-quinuclidinone (2) with the Grignard reagent phenylmagnesium halide, in particular phenylmagnesium bromide or chloride, in the presence of catalytic amounts of copper (I) salts. The copper (I) salts promote the in situ formation of organo-cuprates, allowing to obtain 2-benzhydryl-3-quinuclidinone (1) in high yields.

The reaction is carried out in an aprotic apolar solvent such as 2-methyltetrahydrofuran, toluene, diethyl ether, benzene, preferably 2-methyltetrahydrofuran.

The reaction is carried out in the presence of a copper (I) salt, such as copper (I) chloride, copper (I) bromide, copper (I) iodide, copper (I) oxide, preferably copper (I) iodide, in catalytic amounts ranging from 1% to 7% molar, preferably from 3% to 5% molar to the Grignard reagent.

The process is carried out in an inert environment, preferably under an atmosphere of nitrogen or argon.

The 2-benzylidene-3-quinuclidinone may be used in the solid form, in suspension or in solution in 2-50 volumes of reaction solvent, preferably in 5-20 volumes.

According to a preferred aspect of the invention, the process is carried out as follows. The order of addition of the raw materials can also be different from that reported in the following.

Typically, 1 mole of 2-benzylidene-3-quinuclidinone (2) is reacted with 1-50 moles of Grignard reagent, preferably with 1.2-10 moles, in the presence of an aprotic apolar solvent, preferably 2-methyl-THF. The reaction is carried out in the presence of a copper (I) salt, such as copper (I) chloride, copper (I) bromide, copper (I) iodide, copper (I) oxide, preferably copper (I) iodide, in catalytic amounts ranging from 1% to 7% molar, preferably from 3% to 5% molar to the Grignard reagent.

The reaction is preferably performed at a temperature between −10° C. and 10° C., more preferably between 0 and 5° C.

The reaction is monitored by means of UPLC analysis, typically using a column ACQUITY UPLC® BEH C18 1.7 µm, 2.1X50 mm, with a mixture of water/acetonitrile/0.1% formic acid as eluent phase.

At the end of the reaction, the reaction mixture containing the 2-benzhydryl-3-quinuclidinone (1) is adjusted to a temperature of 0° C.-40° C., preferably 15° C.-25° C., and added to a NH$_4$Cl solution. The diphasic mixture is separated and the organic phase is washed with basic solutions, saline and with water. The organic phase is concentrated to dryness, under vacuum and at a temperature ranging from 25° C. to 90° C., preferably at 40° C.-50° C., and the obtained solid is purified by crystallization from organic solvents, typically selected from methanol, ethanol, isopropanol, propanol, butanol, isobutanol or mixtures thereof, petroleum ether, heptane, hexane, cyclohexane, pentane, toluene, benzene, ethyl acetate, isopropyl acetate, dichloromethane, isopropyl ether, ethyl ether, methyl-tertbutyl-ether, butanone, and acetone, or mixtures thereof. If necessary, the resulting solid can be further purified by recrystallization from solvents typically selected from: water, basic water, methanol, ethanol, acetic acid, isopropanol, propanol, butanol, isobutanol, acetone, butanone, tetrahydrofuran, acetonitrile, and dioxane, or mixtures thereof.

The solid is finally dried under vacuum at a temperature of 30° C.-90° C., preferably at 45° C.-55° C. to obtain the 2-benzhydryl-3-quinuclidinone (1) with purity higher than 99%.

The process of the invention is particularly advantageous in that it allows to obtain the intermediate 2-benzhydryl-3-quinuclidinone (1) in markedly higher yields compared with those reported in the literature, using catalytic amount of copper (I) salts that can be easily disposed of and solvents that are less toxic and expensive than those cited in the state of the art.

The invention is illustrated now in detail by the following examples.

Example 1: Synthesis of
2-benzhydryl-3-quinuclidinone (1)

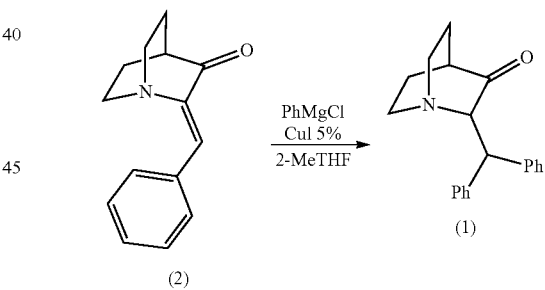

In an inert reactor, 2-methyltetrahydrofuran (2-MeTHF) (55 ml, 11 volumes) and PhMgCl 27.5% w/w in THF (14.05 g, 28.13 mmol) are introduced at room temperature (r.t.). The solution is cooled to 0° C. and at this temperature CuI (5% molar to the Grignard, 0.27 g, 1.42 mmol) is added. The mixture is stirred at 0-2° C. for 10′ and 2-benzylidene-3-quinuclidinone (5 g, 22.51 mmol) is added in portions. After 30′, the reaction is complete.

The resulting solution is allowed to return to r.t. and is slowly dropped over a solution of NH$_4$Cl. The phases are separated and the organic phase is washed twice with NH$_4$OH 20%. The separated organic phase is repeatedly washed with H$_2$O, then it is washed with brine and brought to a residue that is crystallized from EtOH. The resulting white solid is filtered, washed with EtOH and dried. Yield 90%. Purity>99%.

Example 2: Synthesis of 2-benzhydryl-3-quinuclidinone (1)

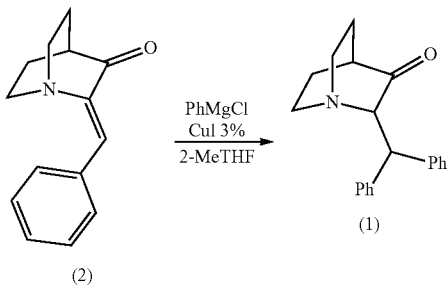

In an inert reactor, 2-MeTHF (3 ml, 6 volumes) and PhMgCl 27.5% w/w in THF (14.05 g, 28.13 mmol) are introduced at r.t.. The solution is cooled to 0° C. and at this temperature CuI (3% molar to the Grignard, 0.16 g, 0.84 mmol) is added. The mixture is stirred at 0-2° C. for 10' and a suspension of 2-benzylidene-3-quinuclidinone (5 g, 22.51 mmol) in 2-MeTHF (27.5 ml, 5.5 volumes) is added in about 30'. After 30', the reaction is complete.

The resulting solution is allowed to return to r.t. and slowly dropped over a solution of NH$_4$Cl. The phases are separated and the organic phase is washed twice with NH$_4$OH 20%. The separated organic phase is repeatedly washed with H$_2$O, then it is washed with Brine and brought to a residue that is crystallized from EtOH. The resulting white solid is filtered, washed with EtOH and dried. Yield 90%. Purity>99%.

Example 3: Synthesis of 2-benzhydryl-3-quinuclidinone (1)

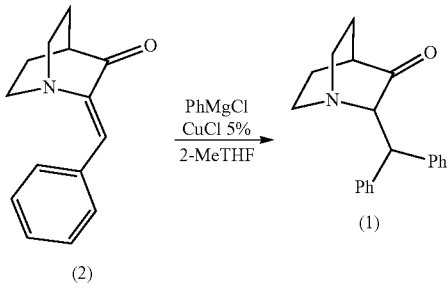 [SMILES: O=C1/C(=C/c2ccccc2)N2CCC1CC2 ; "PhMgBrCul 5%" ; O=C1C2CCN(CC2)C1C(c1ccccc1)c1ccccc1]

In an inert reactor 2-MeTHF (3 ml, 6 volumes) and PhMgCl 27.5% w/w in THF (14.05 g, 28.13 mmol) are added at r.t. The solution is cooled to 0° C. and at this temperature CuCl (5% molar to the Grignard, 0.14 g, 1.42 mmol) is added. The mixture is stirred at 0-2° C. for 10' and a suspension of 2-benzylidene-3-quinuclidinone (5 g, 22.51 mmol) in 2-MeTHF (27.5 ml, 5.5 volumes) is added in about 30'. After 30', the reaction is complete.

The resulting solution is allowed to return to r.t. and slowly dropped over a solution of NH$_4$Cl. The phases are separated and the organic phase is washed twice with NH$_4$OH 20%. The separated organic phase is repeatedly washed with H$_2$O, then it is washed with Brine and brought to a residue that is crystallized from EtOH. The resulting white solid is filtered, washed with EtOH and dried. Yield 85%. Purity>99%.

Example 4: Synthesis of 2-benzhydryl-3-quinuclidinone (1)

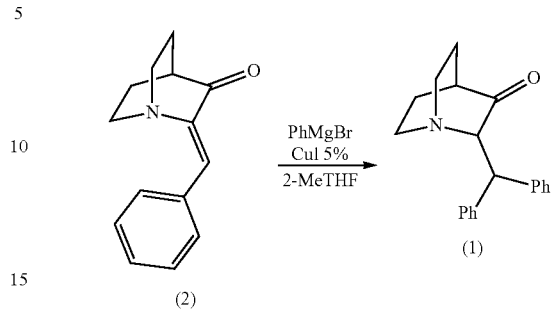

In an inert reactor 2-MeTHF (55 ml, 11 volumes) and PhMgBr 45% w/w in 2-MeTHF (11.33 g, 28.12 mmol) introduced. The solution is cooled to 0° C. and at this temperature CuI (5% molar to the Grignard, 0.27 g, 1.42 mmol) is added. The mixture is stirred at 0-2° C. for 10' and 2-benzylidene-3-quinuclidinone (5 g, 22.51 mmol) is added in portions. After 30', the reaction is complete.

The resulting solution is allowed to return to r.t. and slowly dropped over a solution of NH$_4$Cl. The phases are separated and the organic phase is washed twice with NH$_4$OH 20%. The separated organic phase is repeatedly washed with H$_2$O, then it is washed with Brine and brought to a residue that is crystallized from EtOH. The resulting white solid is filtered, washed with EtOH and dried. Yield 88%. Purity>99%.

Example 5: Synthesis of 2-benzhydryl-3-quinuclidinone (1)

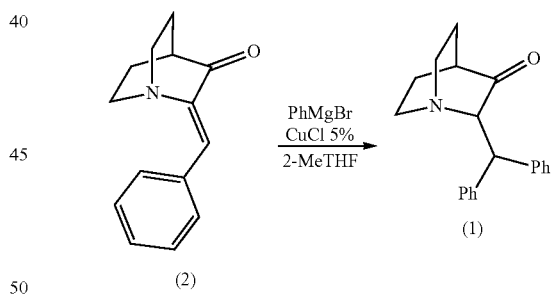

In an inert reactor 2-MeTHF (55 ml, 11 volumes) and PhMgBr 45% w/w in 2-MeTHF (11.33 g, 28.12 mmol) are added. The solution is cooled to 0° C. and at this temperature CuCl (5% molar to the Grignard, 0.14 g, 1.42 mmol) is added. The mixture is stirred at 0-2° C. for 10' and 2-benzylidene-3-quinuclidinone (5 g, 22.51 mmol) is added in portions. After 30', the reaction is complete.

The resulting solution is allowed to return to r.t. and slowly dropped over a solution of NH$_4$Cl. The phases are separated and the organic phase is washed twice with NH$_4$OH 20%. The separated organic phase is repeatedly washed with H$_2$O, then it is washed with Brine and brought to a residue that is crystallized from EtOH. The resulting white solid is filtered, washed with EtOH and dried. Yield 80%. Purity>99%.

The invention claimed is:

1. Process for the preparation of 2-benzhydryl-3-quinuclidinone consisting of reacting 2-benzylidene-3-quinuclidinone in an aprotic apolar solvent with the Grignard reagent phenylmagnesium chloride in the presence of catalytic amounts of copper (I) salts selected from the group consisting of copper (I) bromide, copper (I) iodide and copper (I) oxide and wherein the reaction time is approximately 30 minutes and occurs at temperatures between −10° and +10° C.

2. The process according to claim 1 wherein the solvent is selected from 2-methyltetrahydrofuran, toluene, diethyl ether and benzene.

3. The process according to claim 2 wherein the solvent is 2-methyltetrahydrofuran.

4. The process according to claim 1 wherein the copper (I) salt is copper (I) iodide.

5. The process according to claim 1 wherein the copper (I) salt is present in amounts ranging from 1% to 7% molar to phenylmagnesium chloride halide.

6. Process for the preparation of 2-benzhydryl-3-quinuclidinone consisting of reacting 2-benzylidene-3-quinuclidinone in an aprotic apolar solvent with the Grignard reagent phenylmagnesium chloride halide in the presence of catalytic amounts of copper (I) salts selected from the group consisting of copper (I) bromide, copper (I) iodide and copper (I) oxide, The process according to claim 1 wherein the reacting step is carried out under nitrogen or argon atmosphere, and wherein the reaction time is approximately 30 minutes and occurs at temperatures between −10° and +10° C.

7. The process according to claim 5 wherein the copper (I) salt is present in amounts ranging from 3% to 5% molar to phenylmagnesium chloride.

* * * * *